United States Patent [19]

Zamora

[11] Patent Number: Plant 6,473

[45] Date of Patent: Dec. 20, 1988

[54] *HIBISCUS ROSA-SINENSIS* CV. MONORA

[76] Inventor: Jesus Zamora, 940 W. Hollyvale, Azusa, Calif. 91702

[21] Appl. No.: 855,332

[22] Filed: Apr. 24, 1986

[51] Int. Cl.[4] ..... A01H 5/00
[52] U.S. Cl. ..... Plt./54
[58] Field of Search ..... Plt./54

*Primary Examiner*—Robert E. Bagwill

[57] ABSTRACT

A new and distinct selection of *Hibiscus rosa-sinensis*$_L$. shrub (popularly known as Hibiscus) which shall be referred to hereinafter as *Hibiscus rosa-sinensis* cultivar Monora. *Hibiscus rosa-sinensis* cultivar Monora differs distinctively from other Hibiscus by a unique combination of large white single flowers, floriferous habit, dark green foliage, compact growth habit and high rooting percentages during propagation.

1 Drawing Sheet

DISCOVERY

This invention relates to a new and distinct selection of *Hibiscus rosa-sinensis,* a member of the Malvaceae or mallow family. *Hibiscus rosa-sinensis* cv. Monora was discovered by me in a group of *Hibiscus rosa-sinensis* 'Bride' at Monrovia Nursery Company, 18331 E. Foothill Boulevard, Azusa, Calif. in November, 1981. The plant to date is known to exist only within the boundaries of the Monrovia Nursery and has not been offered for sale or described in any publication.

REPRODUCTION

My new selection has been strictly asexually reproduced by cuttings at Monrovia Nursery Company. The distinct phenotypic characteristics of this new selection that set this plant apart from other hibiscus plants could be lost genetically through sexual reproduction. Therefore, sexual reproduction is prohibited and propagation is restricted to asexual reproduction by cuttings. Seed progeny from the new selection has not been observed.

BRIEF DESCRIPTION OF THE DRAWINGS

The accompanying illustrations show a typical specimen of the plant according to this invention and are depicted in color as nearly true as possible. FIG. 1, shows the original cultivar my improved plant was discovered from. The original cultivar exhibits a size and form similar to my improved selection, however the pure white petals set my selection apart. FIG. 2, depicts a close up of the large 13.5 centimeter (5¼ inch) diameter pure white flowers.

DESCRIPTION

Below is a detailed description of the new *Hibiscus rosa-sinensis* cv. Monora, the color terminology is from the British Horticultural Colour Charts.

Overall size and habit: Evergreen foliage, dense growth, after 2 years plant is 4 ft.×4 ft. After 5 years 5–6 feet with a spread of 4–5 feet.

Flower: Floriferous habit in Southern California from May to October.

- *Size.*—13 cm to 15 cm in diameter.
- *Texture.*—Medium to light texture.
- *Form.*—Single, overlapping petals forming a circular outline.
- *Color.*—White — not located on color chart.
- *Stigma pad color.*—Orpiment Orange 10/3.
- *Style.*—Approximately 9 cm in length, Barium Yellow 503/3.
- *Calyx.*—5 Lobed, 3.5 cm in length.
- *Epicalyx.*—Approximately 8 segments 1.4 cm–2.1 cm.
- *Pedicel length.*—Approximately 6 cm.

Foliage:

- *Size.*—Width 6–10 cm; Length 8.5 cm–11 cm.
- *Shape.*—Cordate.
- *Color.*—Upper: Parsley Green 00962. Lower: Spinach Green 0960/1.
- *Margins.*—Crenate.
- *Texture.*—Coriaceous.
- *Arrangement.*—Alternate.
- *Pubescence.*—Upper: Lightly pubescent. Lower: Pubescent.
- *Petiole.*—2 cm to 3 cm in length.

I claim:

1. A new and distinct selection of *Hibiscus rosa-sinensis* as substantially shown and described herein, that is characterized particularly as a novelty by the unique combination of large white single flowers, floriferous habit, dark green foliage, compact growth habit and high rooting percentages during propagation.

* * * * *

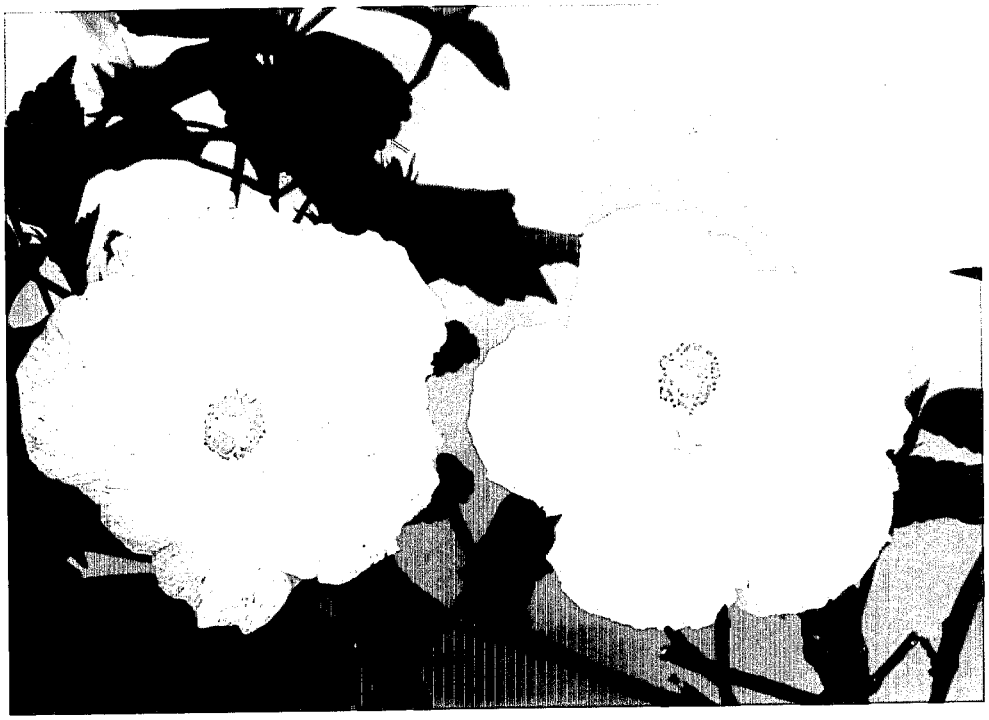
FIG. 1 PRIOR ART & SELECTION
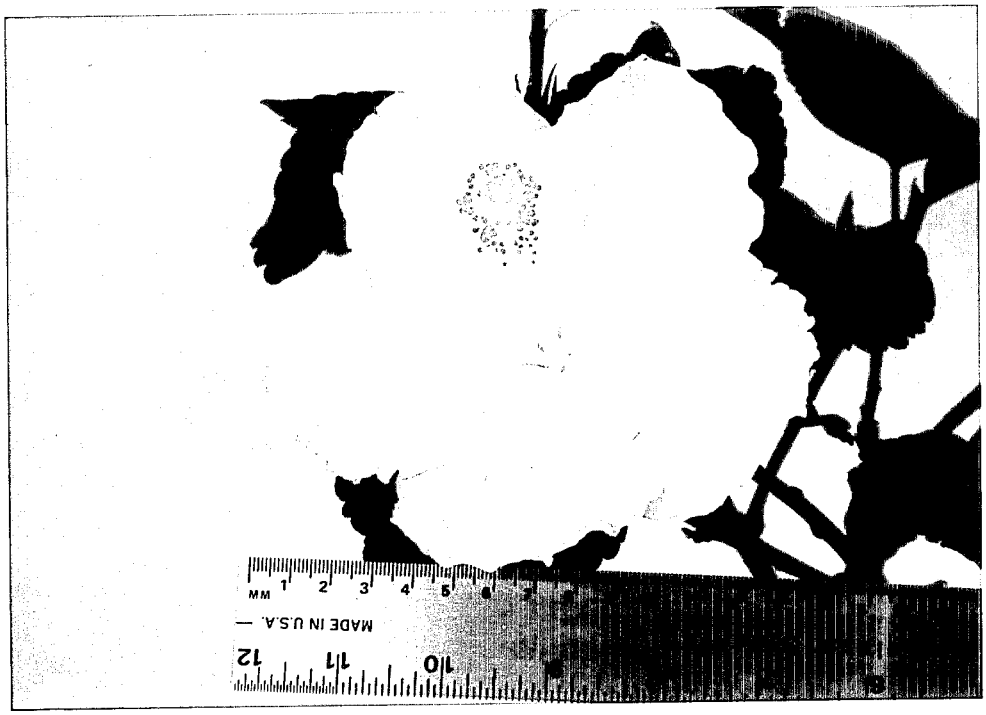
FIG 2 SELECTION